(12) United States Patent
Bütikofer et al.

(10) Patent No.: US 8,608,740 B2
(45) Date of Patent: Dec. 17, 2013

(54) BOLT FOR USE WITH AN EXTERNAL FIXATOR

(75) Inventors: Manfred Bütikofer, Aetingen (CH); Joël Bouquet, Solothurn (CH); Philippe Lehmann, Lamboing (CH)

(73) Assignee: Stryker Trauma SA (CH)

( * ) Notice: Subject to any disclaimer, the term of this patent is extended or adjusted under 35 U.S.C. 154(b) by 0 days.

(21) Appl. No.: 13/180,916

(22) Filed: Jul. 12, 2011

(65) Prior Publication Data

US 2012/0053584 A1 Mar. 1, 2012

(30) Foreign Application Priority Data

Aug. 27, 2010 (EP) .................................. 10174314
Jun. 10, 2011 (EP) .................................. 11169440

(51) Int. Cl.
*A61B 17/60* (2006.01)

(52) U.S. Cl.
USPC ............................................................ 606/59

(58) Field of Classification Search
USPC ............ 606/54–59, 267–272, 277, 286–296, 606/301–321, 324
See application file for complete search history.

(56) References Cited

U.S. PATENT DOCUMENTS

| 4,244,360 A * | 1/1981 | Dohogne .......................... 606/59 |
| 4,870,957 A * | 10/1989 | Goble et al. ................ 623/13.12 |
| 5,053,034 A * | 10/1991 | Olerud .......................... 606/246 |
| 5,306,275 A * | 4/1994 | Bryan ............................ 606/914 |
| 5,451,225 A * | 9/1995 | Ross et al. ....................... 606/59 |
| 5,630,814 A * | 5/1997 | Ross et al. ....................... 606/59 |
| 5,681,309 A | 10/1997 | Ross, Jr. et al. |
| 5,746,741 A | 5/1998 | Kraus et al. |
| 5,921,985 A * | 7/1999 | Ross et al. ....................... 606/59 |
| 6,113,600 A | 9/2000 | Drummond et al. |
| 6,217,578 B1 | 4/2001 | Crozet et al. |
| 6,533,785 B1 | 3/2003 | Frigg et al. |
| 2005/0234450 A1* | 10/2005 | Barker .............................. 606/61 |
| 2006/0247622 A1 | 11/2006 | Maughan et al. |
| 2006/0247629 A1 | 11/2006 | Maughan et al. |
| 2008/0195122 A1* | 8/2008 | Castellvi et al. .............. 606/151 |
| 2009/0228006 A1 | 9/2009 | Mussolin et al. |
| 2010/0160965 A1* | 6/2010 | Viker ............................ 606/246 |

FOREIGN PATENT DOCUMENTS

WO 2009/004347 A1 1/2009

OTHER PUBLICATIONS

Search report of EP 10174314 dated Feb. 11, 2011.

* cited by examiner

*Primary Examiner* — Jerry Cumberledge
(74) *Attorney, Agent, or Firm* — Lerner, David, Littenberg, Krumholz & Mentlik, LLP

(57) ABSTRACT

A bolt is adapted to clamp a pin to an external fixator system. The bolt includes a shaft having a threaded section, a head section and a pin opening that is arranged opposite the threaded section and accommodates and clamps a pin or a wire to a plate or ring of an external fixator. The plate comprises at least one opening which accommodates the shaft and a surface against which the pin or the wire is clamped by the bolt. The pin opening comprises at least two edges extending essentially along the same direction as the pin opening such that the pin or wire to be clamped is contact with said edges.

22 Claims, 3 Drawing Sheets

BOLT FOR USE WITH AN EXTERNAL FIXATOR

CROSS-REFERENCE TO RELATED APPLICATIONS

This application claims the benefit of European Patent Application No. 10174314.4 filed Aug. 27, 2010 and European Patent Application No. 11169440.2 filed Jun. 10, 2011, the disclosures of which are hereby incorporated herein by reference.

BACKGROUND OF THE INVENTION

The present invention relates to a bolt or pin clamp for use with an external fixator.

Currently, there are many bone deformities or fractures that external fixators can correct. Such devices such as those designed by Illzarov for example. Usually such an external fixator comprises rings or plates also designated as fixation plates connected by threaded rods or struts to manipulate angulations, translation and length discrepancies of bones. Furthermore the fixation plates are connected to bony structure by means of pins which usually extend through the rings. The pins are connected to the plates by means of bolts and nuts. Usually pins having different diameters will be used depending on the special situation near the fracture. For that reason several bolts with openings having respective diameters have to be used.

U.S. Pat. Nos. 5,630,814 and 5,681,309 provide one solution to adapt a bolt in order to be used to clamp different pin or wire sizes. For that reason the bolt comprises an opening which is provided with cross section that is tear drop-shaped. Thereby the pin is in connection with the bolt and the fixation plate via three contact zones all of which are provided with respective surfaces.

The shape of the drop shaped opening as well as the fact that the pin is clamped via plane surfaces has several drawbacks. Due to the shape it may be possible that it comes to gaping such that the sidewalls of the opening will be moved with respect to each other. Furthermore it is possible that the area above the opening fractures in case extraordinary tightening forces are necessary.

BRIEF SUMMARY OF THE INVENTION

It is therefore one aspect of the present invention to provide a bolt to clamp pins with different diameters to an external fixator. In particular the process of tightening a pre-aligned pin shall, as well as the connection between the pin and the bolt, shall be improved.

Such an aspect is achieved by a bolt that is adapted to clamp a pin to an external fixator system which comprises a shaft having a threaded section, a head section and a pin opening that is arranged opposite the threaded section and accommodates and clamps a pin or a wire to a plate of an external fixator. The plate comprises at least one opening which accommodates the shaft and a surface against which the pin or the wire is clamped by means of the bolt, in particular by means of the pin opening. The pin opening comprises at least two edges extending essentially along the same direction as the pin opening such that the pin or wire to be clamped is in contact with the edges. The pin is thereby clamped with the edges and the surface of the plate. Preferably the edges are arranged at a distance from each other.

Because of the arrangement of the edges it is possible to clamp wires or pins with different diameters. Furthermore the edges improve the clamping connection as higher forces can be carried. As the bolt is moved along its middle axis towards the surface of the plate the pin can be pre-aligned and its orientation will not change during tightening of the bolt. Preferably the pin opening comprises exactly two edges, which allows centering the pin or wire in an automatic manner. Preferably the pin opening is limited by a surface, wherein the edges extend from said surface or wherein the edges are part of the surface.

Preferably the pin opening comprises a groove extending from the surface of the pin opening into the bolt such that two edges will be provided. Thereby the edges are part of the surface of the pin opening. Such a structure can be manufactured very efficiently.

Alternatively the edges have the shape of a ridge which extends from the surface into the inner width of the pin opening.

Preferably the edges extend only partly over the length of the pin opening and/or the edges are interrupted over the length of the pin opening. Thereby one edge comprises several sections which are arranged in a line one behind the other.

Preferably the shaft extends along a middle axis and the edges extend angular to the middle axis such that the distance as viewed perpendicular to the middle axis remains constant. Preferably the pin opening has a circular cross-section opposite the edges, such that the pin or wire will be centred before tightening.

Preferably the bolt comprises a shaft section that is arranged between the threaded section and the head section, wherein the pin opening is arranged such that its cross-section extends into the head section and into the shaft section. Preferably the pin opening is arranged such that its cross-section extends into the head section and into the threaded section.

An external fixator system comprising at least one fixation plate with a plurality of openings and at least one pin to be attached to the fixation plate, wherein the pin is attached by means of a bolt as described above and by means of a corresponding nut, wherein the bolt extends through said opening in the plate and clamps the pin by means of said pin opening with the edges and a surface of the fixation plate.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DETAILED DESCRIPTION

Figure 1:
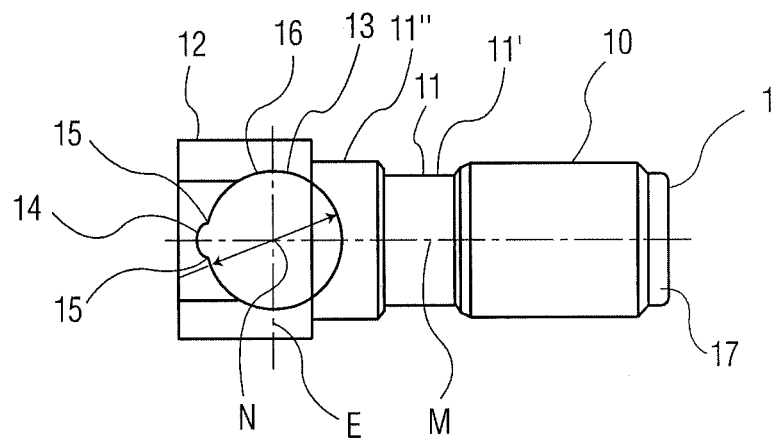
FIG. 1 shows a side view of the bolt for use with an external fixator.
Figure 2:
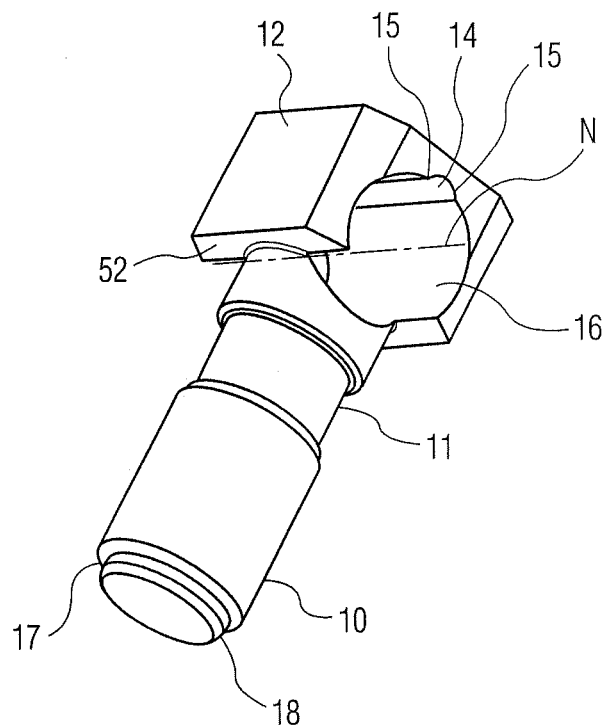
FIG. 2 shows a perspective view of the bolt according to FIG. 1.

Referring to FIGS. 1 and 2 there is shown a bolt 1 or a screw for clamping a wire or a pin to a fixation plate 3 in an external fixator system. The bolt 1 extends along a middle axis M and comprises a shaft having a threaded section 10, a head section 11 and a pin opening 13. The pin opening 13 serves to accommodate and to clamp a pin 2 or a wire to an external fixator.

Figure 3:
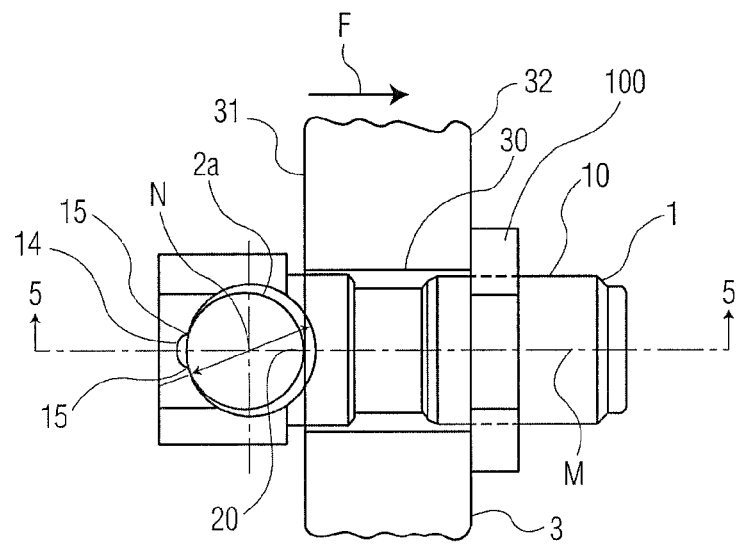
FIG. 3 shows a side view of an assembly of the bolt according to FIG. 1 with a pin and a schematic view of a fixation plate.

The bolt 1 extends through an opening 30 in a fixation plate or ring 3 as seen in FIG. 3. The opening thereby extends from a top surface 31 to a bottom surface 32. The bolt 1 is attached by means of a nut which comes into contact with the bottom surfaces 32. Upon tightening the nut the bolt 1 will be moved with its head section 11 along the middle axis M towards the top surface 31 whereupon the pin 2 will be clamped by means of the pin opening 13 and the top surface 31. This will be further explained below with FIGS. 3 and 4.

With regard to FIGS. 1 and 2 the pin opening 13 will now be explained in greater detail. The pin opening 13 extends along a middle axis N preferably perpendicular to axis M and has substantially a circular cross-section. The pin opening 13 comprises an inner surface 16 defining said pin opening. Furthermore the pin opening 13 comprises at least two edges 15 which preferably extend in substantially the same direction as the pin opening itself, namely along or parallel to middle axis N. When a pin 2 or wire will be clamped it is in contact via said edges 15 with the pin opening. Preferably exactly two edges 15 are provided. In this regard it has to be noted that the term "edge" includes everything that it is arranged aligned in the respective direction. In case the edge is subdivided or interrupted along its length this is still to be considered as one edge with multiple sections. In a preferred embodiment the edges 15 have the same length as the pin opening 13 such that uninterrupted edges 15 can be provided.

The edges 15 can be arranged such that they are part of the surface 16 as it is shown in the figures. Thereby the edges 15 are provided by means of a channel or groove 14 which extends from the surface 16 of the pin opening 13 into the bolt 1. Preferably the groove 14 has a cross-section of a semicircle as such a structure can be manufactured very easily. However, other cross-sections such as rectangular or polygonal may also be possible.

Alternatively the edges 15 can also be provided such that they extend from the surface 16 into the pin opening 13. This means that separate edge elements 15 such as ridges extending from the surface 16 of said pin opening 13.

The edges 15 extend preferably over the whole length of the pin opening 13 without an interruption. Hence there is a contact with the pin that is inserted into the pin opening 13 over the whole length of that part of the pin that extends into the opening. In view of the top surface it has to be noted that the pin is in contact with the top surface in the area that surrounds the opening 30 in the plate 3. In this regard it is preferable that the head section 12 is larger in direction of the middle axis N than the diameter of the opening 30 so that the edges 15 extend over the opening 30 when viewed along middle axis M. With other words: the pin opening 13 is therefore larger than the diameter of the opening 30 in the plate. Therefore the part of the pin which is arranged between the edges 15 of groove and the surface 31 as viewed along middle axis M is in contact with the edges 15 of groove 14 of the pin 1 as well as with the plate 3. This enhances the clamping connection between the pin 1 and the plate 3. Furthermore bending of the pin 1 can be prevented. At no time will a bottom surface 52 of head section 12 contact top surface 31 of plate or ring 3.

However, it may also be possible that the edges 15 extend only over parts of said pin opening 13 or that the edges are partly interrupted. Thereby each of the edges 15 would comprise a plurality of edged pieces which are arranged collinear to each other in order to provide said edges 15. Alternatively an edge 15 may also be provided by means of several embossments which are also arranged one behind the other.

Preferably the edges 15 extend in substantially the same direction as the pin opening 13, namely parallel to middle axis N. A virtual plane E that extends perpendicular to the middle axis N of the bolt 1 as well as the middle axis M itself are used in the following to define the position of the edges 15. The virtual plane E is substantially parallel to the top surface 31 of the external fixator. Both edges 15 are arranged at the same distance from the virtual plane E and also at the same distance from the middle axis M. Thereby the pin can be arranged in a very stable and well defined manner. The width of the head along plane E is preferably greater than the diameter of hole 30

Alternatively to a collinear arrangement to the edges 15 to the middle axis N, the edges 15 can also be arranged at an angle to the middle axis N so that the edges 15 extend at a constant distance perpendicular to the middle axis M, i.e. in a common plane which is parallel to virtual plane E, but angular with respect to the middle axis. Thereby it is possible that the edges 15 cross or touch each other somewhere in the opening 13.

The bolt can additionally have a shaft section 11 which is arranged between the threaded section 10 and the head section 12. The shaft section can have a constant diameter or it may comprises a first portion 11' and a second portion 11" with different diameters. In the embodiment according to the figures the first portion 11' adjoining the threaded section 10 has a smaller diameter than the second portion 11". It may also be possible to arrange the portion with the larger diameter next to the threaded portion 10 and the portion with the smaller diameter next to the head portion 12.

The threaded section 10 may also include a shaft part having a chamfered edge 18 which allows a very easy positioning within the opening 30. The pin opening 13 is arranged such that it extends within the head section 12 and also with then shaft section 11 and/or the threaded section 10.

The head section 12 has substantially a cubic shape so that the head section is graspable by means of a tool such as a wrench in order to provide a counter-torque when a nut 50 is tightened.

Figure 4:
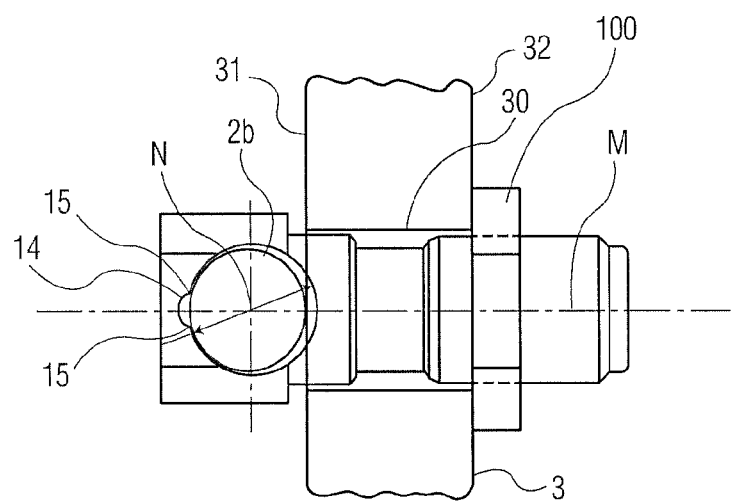
FIG. 4 shows a side view of the bolt according to FIG. 1 with a pin and a schematic fixation plate.
Figure 5:
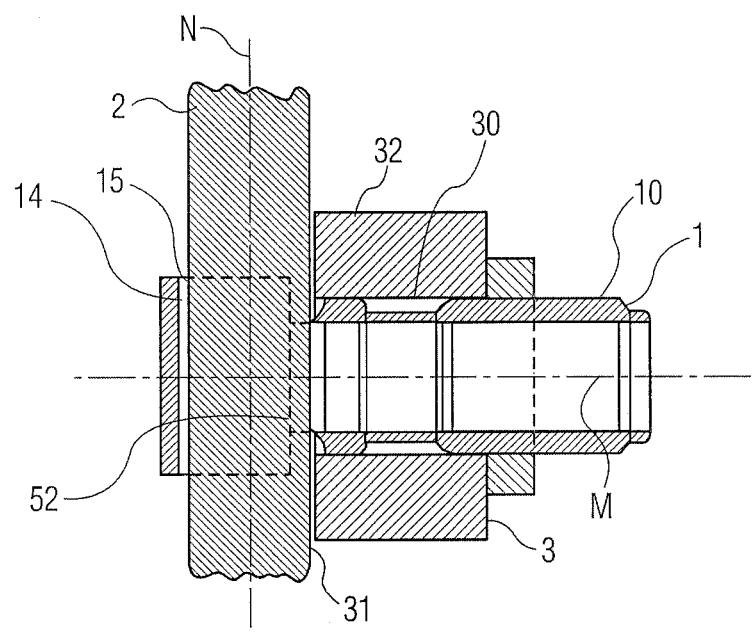
FIG. 5 shows a cross-sectional view of the assembly of FIG. 3 along lines 5-5.
Figure 6:
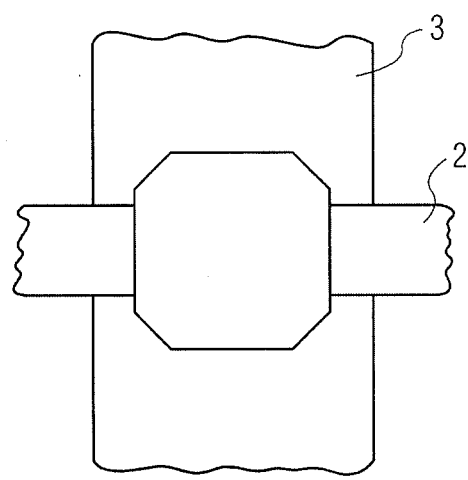
FIG. 6 is a top view of the assembly of FIG. 3.

Reference is now made to FIGS. 3-6 which show a pin 2a in FIGS. 3 and 2b in FIG. 4 within the pin opening 13 whereby the pin will be clamped by means the bolt 1 and nut 50 to the fixator plate 3. The nut 50 is in connection with the threaded section 10 of the bolt. Upon tightening the nut a force F acts onto the bolt 1 and it will be moved with the head section 12 towards the top surface 31 of the fixator plate 3. The movement of the bolt 1 is collinear to the middle axis M of the opening 30 in plate 3. As the counter torque can be compensated by means of a tool that engages head section 12 there will be no rotation of the bolt 1 while tightening nut 50. Furthermore due to movement of the bolt 1 along the middle axis no torque will be applied onto pins 2a or 2b and therefore the arrangement has the advantage that the pin 2 can be aligned before tightening and during the tightening process the alignment of the pins 2a, 2b will not be disturbed. Hence the pins 2a, 2b are mainly in contact with elements, namely the edges 15 and surface 30 that move parallel to each other. Thereby the pins 2a, 2b will be clamped by means of the edges 15 and by means of the top surface 31. The surface 20 of the pins 2a, 2b is therefore in contact with the top surface 31 and with the edges 15. Hence the pins 2a, 2b will be clamped at every cross-section at three different positions which means that the pin 2 will be automatically centered within the opening and therefore a reliable connection can be established.

Due to the arrangement of the edges 15 it is also possible to clamp pins with different diameters, since the edges 15 are arranged such that they are always in contact with the surface 20 of the pin, irrespective of its diameter. In the case of pin 2a with a smaller diameter shown in FIG. 4 the bottom surface 52 of bolt 1 will be moved closer to the top surface 31 of the fixation plate 3.

The central axis of the pin is, depending on the diameter of the pin, is shifted or offset from the middle axis N of the opening 16. The pin itself is however always in contact with the top surface 31 of the fixation plate 3 which means that the pin central axis is always arranged on the same plane along middle axis M irrespective of its diameter. The pin 2 is therefore always in contact with the top surface 31 of the fixation plate 3 at a point which is shown with reference numeral 20.

It has to be noted that the pin 2 is in contact with the external fixator by means of its surface which contacts the edges 15 and the top surface 31. Thereby three contact zones are established.

The bolt 1 with the pin opening 16 and the edges 15 has the advantage that it is possible to clamp pins with different diameter whereby the contact zones between the pin 2 and the bolt 1 remain at the same position. This means that it is possible to provide reproducible connections between the pin and the bolt. Furthermore the same tightening force can be applied in order to achieve constant clamping force onto the pin.

Furthermore it is also possible to provide the edges 15 such that they impinge into the surface of the wire or pin which means that a higher clamping force will be achieved.

The circular cross-section of the pin opening 13 is particularly advantageous as the pin 2 is centred with the section of the opening 13 opposite the edges 15. Upon tightening the pin 2 then comes into contact with the edges 15 which ensure that the pin is aligned accordingly. This means the pin is pre-aligned by means of the circular pin opening 13 before it will be clamped.

The bolt is preferably made out of metal preferably such as stainless steel, titanium or aluminium.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An external fixator system comprising
at least one fixation plate having an upper surface, a lower surface and at least one opening extending through said plate from the upper surface to the lower surface,
at least one pin or wire to be attached to said fixation plate,
a bolt adapted to attach said pin, said bolt comprising:
a shaft having a threaded section,
a head section and
a pin opening that is arranged opposite the threaded section and is adapted to accommodate and to clamp the pin or wire to said plate, said pin opening having at least two edges extending essentially along the same direction as the pin opening such that the pin or wire to be clamped is in contact with said edges,
wherein said edges are arranged within said opening
and a nut which corresponds to the threaded section of the bolt;
wherein the bolt extends through said opening in the plate and clamps the pin or wire by means of said pin opening with the edges and a surface of the fixation plate; and
wherein the pin or wire is in direct contact with said surface of said plate.

2. The external fixator system according to claim 1, wherein the pin opening comprises exactly two edges.

3. The external fixator system according to claim 1, wherein said edges extend over the whole length of the pin opening.

4. The external fixator system according to claim 1, wherein the pin opening is limited by a surface, wherein the edges extend from said surface or wherein the edges are part of said surface.

5. The external fixator system according to claim 1, wherein the pin opening comprises a groove extending from the surface of the pin opening into the bolt such that two edges will be provided.

6. The external fixator system according to claim 5, wherein said groove has the cross-section of a semi-circle.

7. The external fixator system according to claim 1, wherein said edges have the shape of a ridge which extends from the surface into the inner width of the pin opening.

8. The external fixator system according to claim 1, wherein the edges extend only partly over the length of the pin opening and/or in that the edges are interrupted over the length of the pin opening.

9. The external fixator system according to claim 1, wherein the shaft extends along a middle axis and in that the edges extend angular to the middle axis such that the distance from the middle axis to each of the edges as viewed perpendicular to the middle axis remains constant.

10. The external fixator system according to claim 1, wherein the bolt comprises an intermediate shaft section that is arranged between the threaded section and the head section, wherein the pin opening is arranged such that its cross-section extends into the head section and into the intermediate shaft section.

11. The external fixator system according to claim 1, wherein the shaft section comprises a first portion and a second portion, wherein the first portion adjoining the threaded section has a smaller diameter than the second portion.

12. The external fixator system according to claim 1, wherein the pin opening is arranged such that its cross-section extends into the head section and into the threaded section.

13. The external fixator system according to claim 1, wherein the pin opening extends along a middle axis which is substantially perpendicular to the middle axis of the bolt.

14. The external fixator system according to claim 1, wherein the pin opening is arranged such that it extends within the head section and also within the shaft section and/or the threaded section.

15. The external fixator system according to claim 1, wherein the pin opening has a length along its middle axis that is larger than the diameter of the opening of the fixation plate, such that said edges extend over the diameter of the opening.

16. An external fixator system comprising
at least one fixation plate having a planar upper surface, a lower surface and at least one opening extending through said plate from the upper surface to the lower surface,
at least one pin or wire to be attached to said fixation plate,
a bolt adapted to attach said pin, said bolt comprising:
a shaft extending along a first axis having a threaded section,
a head section having a cross-section forming the largest cross-section of the bolt and
a pin opening extending entirely through the head section that is arranged along a second axis opposite the threaded section and is adapted to accommodate and to clamp the pin or wire to said plate, said pin opening has a recessed portion forming two edges extending in parallel in the same direction as the second axis such that the pin or wire to be clamped is in contact with said edges, the at least two edges extending entirely through the head section, the pin or wire having a surface contacting the fixation plate planar upper surface;

and a nut which corresponds to the threaded section of the bolt, the nut contacting the fixation plate lower surface;

wherein the bolt extends through said opening in the plate and clamps the pin or wire by means of said pin opening with the edges and a surface of the fixation plate.

17. The external fixator system according to claim 16, wherein said edges extend over the whole axial length of the pin opening.

18. The external fixator system according to claim 16, wherein the pin opening comprises a groove extending from the surface of the pin opening into the bolt such that two edges will be provided.

19. The external fixator system according to claim 18, wherein said groove has the cross-section of a semi-circle.

20. The external fixator system according to claim 16, wherein said edges have the shape of a ridge which extends from the surface into the pin opening.

21. The external fixator system as set forth in claim 16 wherein the edges extend in parallel at a constant distance from the second axis.

22. An external fixator system comprising at least one fixation plate having a planar upper surface, a lower surface and at least one opening extending through said plate from the upper surface to the lower surface, at least one pin or wire to be attached to said fixation plate, a bolt adapted to attach said pin, said bolt comprising:

a shaft having a threaded section, a head section having a cross-section forming the largest cross-section of the shaft, and a pin opening extending entirely through the head section that is arranged opposite the threaded section and is adapted to accommodate and to clamp the pin or wire to said plate, said pin opening having at least two edges extending in parallel entirely across the pin opening in the same direction as the pin opening such that the pin or wire to be clamped is in contact with said edges and in contact with the fixation plate planar upper surface and a nut which corresponds to the threaded section of the bolt contacting the lower surface of the fixation plate;

wherein the bolt extends through said opening in the plate and clamps the pin or wire by means of said pin opening between the edges and the planar upper surface of the fixation plate.

* * * * *